US012440834B2

(12) United States Patent
Kauffmann

(10) Patent No.: US 12,440,834 B2
(45) Date of Patent: Oct. 14, 2025

(54) AUTOMATIC LIQUID ANALYTICAL REAGENT DISPENSING APPARATUS, ANALYTICAL ASSAY REACTION CARTRIDGES AND KITS, AND METHODS OF USE RELATED THERETO

(71) Applicant: Siemens Healthcare Diagnostics Inc., Tarrytown, NY (US)

(72) Inventor: Aaron Kauffmann, Elkhart, IN (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 566 days.

(21) Appl. No.: 17/996,669

(22) PCT Filed: Apr. 20, 2021

(86) PCT No.: PCT/US2021/028142
§ 371 (c)(1),
(2) Date: Oct. 20, 2022

(87) PCT Pub. No.: WO2021/216543
PCT Pub. Date: Oct. 28, 2021

(65) Prior Publication Data

US 2023/0211336 A1 Jul. 6, 2023

Related U.S. Application Data

(60) Provisional application No. 63/014,734, filed on Apr. 24, 2020.

(51) Int. Cl.
*B01L 3/00* (2006.01)
*G01N 33/72* (2006.01)

(52) U.S. Cl.
CPC ............ *B01L 3/502* (2013.01); *G01N 33/721* (2013.01); *B01L 2200/16* (2013.01); *B01L 2300/0816* (2013.01); *B01L 2300/0838* (2013.01); *B01L 2300/0858* (2013.01)

(58) Field of Classification Search
CPC ................ B01L 3/502; B01L 2200/16; B01L 2300/0816; B01L 2300/0838; B01L 2300/0858; G01N 33/721
See application file for complete search history.

(56) References Cited

U.S. PATENT DOCUMENTS

| | | | |
|---|---|---|---|
| 5,272,093 | A | 12/1993 | Silva et al. |
| 5,976,469 | A | 11/1999 | Davis |
| 2011/0201099 | A1 | 8/2011 | Anderson et al. |
| 2016/0202275 | A1 | 7/2016 | Bae et al. |

(Continued)

OTHER PUBLICATIONS

International Search Report and Written Opinion of International Application No. PCT/US2021/028142 dated Jul. 8, 2021.

*Primary Examiner* — Jill A Warden
*Assistant Examiner* — Michael Stanley Gzybowski

(57) ABSTRACT

Analytical assay reaction cartridges are disclosed that include a reagent tray containing a liquid reagent disposed therein and a flexible cover removably attached thereto. The flexible cover has a portion that extends beyond the reagent tray and that forms a tab portion extends through an opening in a lid member of the cartridge in order to facilitate removal of at least a portion of the cover and release of the liquid reagent. Also disclosed are analytical assay reaction kits that include the cartridges and diagnostic instruments for use with the analytical assay reaction cartridges/kits, as well as methods of making and using the cartridges/kits.

28 Claims, 8 Drawing Sheets

(56) References Cited

U.S. PATENT DOCUMENTS

| | | | |
|---|---|---|---|
| 2019/0003930 | A1 | 1/2019 | Byrne et al. |
| 2019/0240667 | A1 | 8/2019 | Ledden |
| 2019/0317115 | A1 | 10/2019 | MacLean et al. |
| 2020/0368746 | A1 | 11/2020 | Kauffmann |

AUTOMATIC LIQUID ANALYTICAL REAGENT DISPENSING APPARATUS, ANALYTICAL ASSAY REACTION CARTRIDGES AND KITS, AND METHODS OF USE RELATED THERETO

CROSS REFERENCE TO RELATED APPLICATIONS/INCORPORATION BY REFERENCE STATEMENT

This application claims benefit under 35 USC § 119 (e) of U.S. Provisional Application No. 63/014,734, filed Apr. 24, 2020. The entire contents of the above-referenced patent application are expressly incorporated herein by reference.

STATEMENT REGARDING FEDERALLY FUNDED RESEARCH OR DEVELOPMENT

Not Applicable.

BACKGROUND

Numerous devices and methods exist for detecting analytes that may be present in a patient's biological liquid test sample. Such devices have been proven to be effective in diagnostic assays that detect the presence and/or quantity of certain analytes indicative of a patient's health, including, but not limited to, glycated hemoglobin (HbA1c), microalbumin and creatinine, and lipid-based analytes, such as (but not limited to) cholesterol, triglycerides, and/or high-density lipoproteins. A key component of conducting these various analytical assays is the introduction at least one liquid analytical reagent within a reaction cartridge, that mixes with (and/or dilutes) the patient's biological liquid test sample. Currently, such devices, kits, and methods rely on a user (such as a clinician or laboratory personnel) to manually introduce the at least one liquid analytical reagent into the reaction cartridge—for instance, by removing (via, by way of example, by pulling) a flexible cover so as to remove the flexible cover from a container that holds the at least one liquid analytical reagent. In such cases, the manual removal of the flexible cover may result in reduced and/or incomplete dispensing of the predetermined volume of liquid reagent(s) contained within the previously-sealed container. Such reduced and/or incomplete dispensing can result in imprecise and unwanted errors associated with the analytical measurements obtained from the conductance of the analytical assay(s), for instance, errors resulting from the inaccurate dilution of the patient's liquid biological sample.

Accordingly, there is a need in the art for new and improved devices, kits, and methods that mitigate, if not eliminate, errors resulting from the incomplete and/or imprecise dispensing of at least one liquid analytical reagent from a dispensing apparatus into a reaction chamber of a reaction cartridge for the conductance of one or more analyte detection assays. It is to such devices, kits, and methods that the present disclosure is directed.

DETAILED DESCRIPTION

Figure 1:
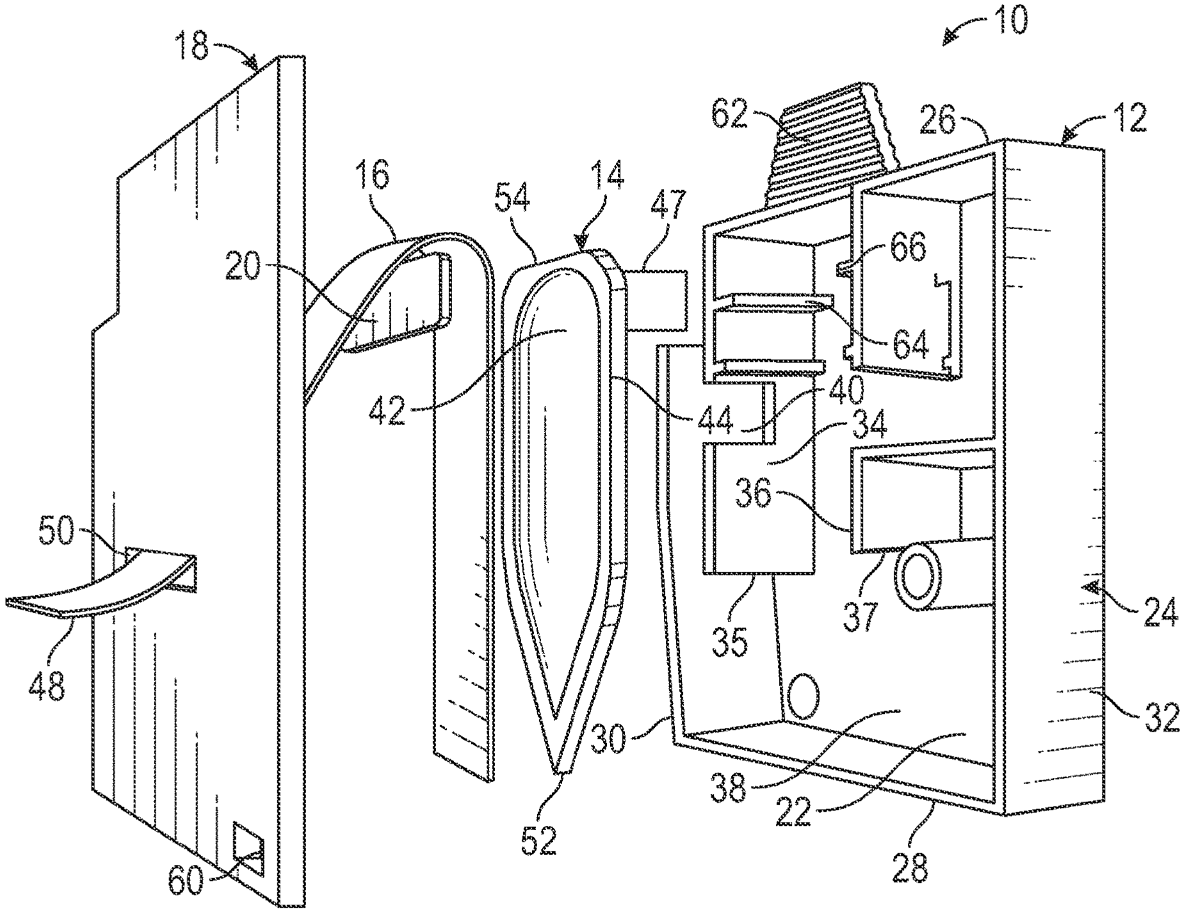
FIG. 1 is an exploded perspective view of a non-limiting embodiment of an analytical assay reaction cartridge constructed in accordance with present disclosure.

Before explaining at least one embodiment of the inventive concept(s) in detail by way of exemplary drawings, experimentation, results, and laboratory procedures, it is to be understood that the inventive concept(s) is not limited in its application to the details of construction and the arrangement of the components set forth in the following description or illustrated in the drawings, experimentation, and/or results. The inventive concept(s) is capable of other embodiments or of being practiced or carried out in various ways. As such, the language used herein is intended to be given the broadest possible scope and meaning, and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the present disclosure shall have the meanings that are commonly understood by those of ordinary skill in the art. Further, unless otherwise required by context, singular terms shall include pluralities, and plural terms shall include the singular. The foregoing techniques and procedures are generally performed according to conventional methods well known in the art and as described in various general and more specific references that are cited and discussed throughout the present specification. The nomenclatures utilized in connection with, and the laboratory procedures and techniques of, analytical chemistry, synthetic organic chemistry, and medicinal and pharmaceutical chemistry described herein are those well-known and commonly used in the art.

All patents, published patent applications, and non-patent publications mentioned in the specification are indicative of the level of skill of those skilled in the art to which the present disclosure pertains. All patents, published patent applications, and non-patent publications referenced in any portion of this application are herein expressly incorporated by reference in their entirety to the same extent as if each individual patent, patent application, or publication was specifically and individually indicated to be incorporated by reference.

All of the devices, kits, and/or methods disclosed and claimed herein can be made and executed without undue experimentation in light of the present disclosure. While the compositions and methods of this present disclosure have been described in terms of particular embodiments, it will be apparent to those of skill in the art that variations may be applied to the devices, kits, and/or methods, and in the steps or in the sequence of steps of the methods described herein, without departing from the concept, spirit, and scope of the present disclosure. All such similar substitutions and modifications apparent to those skilled in the art are deemed to be within the spirit, scope, and concept of the inventive concept(s) as defined by the present disclosure and the appended claims.

As utilized in accordance with the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The singular forms "a," "an," and "the" include plural referents unless the context clearly indicates otherwise. Thus, for example, reference to "a compound" may refer to 1 or more, 2 or more, 3 or more, 4 or more, or greater numbers of compounds. The term "plurality" refers to "two or more." The use of the term "or" in the claims is used to mean "and/or" unless explicitly indicated to refer to alternatives only, or the alternatives are mutually exclusive, although the disclosure supports a definition that refers to only alternatives and "and/or."

Throughout this application, the term "about" is used to indicate that a value includes the inherent variation of error for the device, the method being employed to determine the value, or the variation that exists among the study subjects. For example but not by way of limitation, when the term "about" is utilized, the designated value may vary by ±20%, or ±10%, or ±5%, or ±1%, or ±0.1% from the specified value, as such variations are appropriate to perform the disclosed methods and as understood by persons having ordinary skill in the art.

The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y, and Z" will be understood to include X alone, Y alone, and Z alone, as well as any combination of X, Y, and Z. The use of ordinal number terminology (i.e., "first," "second," "third," "fourth," etc.) is solely for the purpose of differentiating between two or more items and is not meant to imply any sequence or order of importance of one item over another or any order of addition, for example.

As used in this specification and claim(s), the terms "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

As used herein, the phrase "associated with" includes both direct association of two moieties to one another as well as indirect association of two moieties to one another. Non-limiting examples of associations include covalent binding of one moiety to another moiety either by a direct bond or through a spacer group, non-covalent binding of one moiety to another moiety either directly or by means of specific binding pair members bound to the moieties, incorporation of one moiety into another moiety such as by dissolving one moiety in another moiety or by synthesis, and coating one moiety on another moiety.

The term "liquid test sample" as used herein will be understood to include any type of biological fluid sample that may be utilized in accordance with the present disclosure. Examples of biological samples that may be utilized include, but are not limited to, whole blood or any portion thereof (i.e., plasma or serum), saliva, sputum, cerebrospinal fluid (CSF), intestinal fluid, intraperitoneal fluid, cystic fluid, sweat, interstitial fluid, tears, mucus, urine, bladder wash, semen, combinations thereof, and the like. The volume of the liquid test sample utilized in accordance with the present disclosure may be (for example but not by way of limitation) from about 0.1 μl to about 100 μl.

As used herein, the term "volume" as it relates to the liquid test sample utilized in accordance with the present disclosure means from about 0.1 μl to about 100 μl, or from about 1 μl to about 75 μl, or from about 2 μl to about 60 μl, or less than or equal to about 50 μl.

The term "patient" includes human and veterinary subjects. In certain embodiments, a patient is a mammal. In certain other embodiments, the patient is a human. "Mammal" for purposes of diagnosis/treatment refers to any animal classified as a mammal, including human, domestic and farm animals, nonhuman primates, and zoo, sports, or pet animals, such as dogs, horses, cats, cows, etc.

Turning now to particular non-limiting embodiments of the inventive concept(s), the present disclosure is related to improved device(s), kit(s), and method(s) for dispensing a predetermined volume of at least one liquid analytical reagent (such as, but not limited to, at least one buffer solution) for use in conducting one or more analyte detection assays. More specifically, the present disclosure relates to a modified analytical assay reaction cartridge and/or reaction kit that contains an automatic liquid analytical reagent dispensing apparatus (in the form of a flexible cover removably affixed to a reagent tray) that allows for the automatic and substantially complete dispensing of a predetermined volume of at least liquid one analytical reagent from the reagent tray into a reaction chamber upon the modified analytical assay reaction cartridge and/or reaction kit being placed within a suitable diagnostic assay instrument/system, as well as methods of production and use related thereto. The present disclosure also relates to a modified diagnostic instrument for performing the analytical assay, wherein the modified diagnostic instrument contains an actuator for the automatic dispensing of the reagent from the analytical assay reaction cartridge/kit.

Such improved devices, kits, and methods thereby allow for (for example and not by way of limitation): (1) automatic removal of a portion or all of a flexible cover that seals a liquid reagent-holding tray that is integrated and housed in an analytical assay reaction cartridge of an analytical assay reaction kit—the flexible cover being automatically removed upon insertion of the analytical assay reaction cartridge/kit into a suitable diagnostic assay instrument/system; (2) the dispensing of substantially the entire predetermined volume of the liquid reagent from the reagent tray into the reaction chamber of the reaction cartridge/kit; and (3) an increase in the precision of measurements obtained from conducting a diagnostic assay(s) on a patient's biological liquid test sample resulting from mixing the patient's biological liquid test sample with the predetermined volume of the liquid analytical reagent.

It is contemplated that virtually any reagent used in the fields of biological, chemical, or biochemical analyses and assays could be used in the devices, kits, and methods of the present disclosure. It is contemplated that, in certain non-limiting embodiments, these reagents may undergo physical and/or chemical changes when bound to an analyte of interest whereby the intensity, nature, frequency, and/or type of signal generated by the reagent-analyte complex is directly proportional or inversely proportional to the concentration of the analyte existing within the fluid sample. These reagents may contain (for example, but not by way of limitation) indicator dyes, metal, enzymes, polymers, antibodies, and electrochemically reactive ingredients and/or chemicals that, when reacting with an analyte(s) of interest, may exhibit a change in color. In addition, another non-limiting example of an analytical reagent is a buffer. In yet another, non-limiting example, the analytical reagent can be a solvent or solution in which a solid analytical reagent present in the reaction chamber can be dissolved or suspended.

Any method of detecting and/or measuring an analyte in a fluid sample can be used in the devices, kits, and methods of the present disclosure. A variety of assays for detecting analytes are well known in the art and include, but are not limited to, chemical assays, enzyme inhibition assays, antibody stains, latex agglutination, latex agglutination inhibition, and immunoassays such as (but not limited to) radioimmunoassays.

The term "antibody" herein is used in the broadest sense and refers to, for example, intact monoclonal antibodies, polyclonal antibodies, multi-specific antibodies (e.g., bispecific antibodies), and to antibody fragments that exhibit the desired biological activity (e.g., antigen/analyte-binding). The antibody can be of any type or class (e.g., IgG, IgE, IgM, IgD, and IgA) or sub-class (e.g., IgG1, IgG2, IgG3, IgG4, IgA1, and IgA2).

While immunoassays (including, but not limited to, sequential analytical chemical and immunoassays) are primarily discussed herein for the detection of at least one analyte of interest present in a liquid test sample, a person having ordinary skill in the art should readily understand that the present disclosure is not strictly limited to immunoassays and may include, by way of example and not by limitation, chemical and chemical-based assays, nucleic acid assays, lipid-based assays, and serology-based assays. Immunoassays (such as, but not limited to, radioimmunoassays and enzyme-linked immunoassays) are useful methods for use with the present disclosure. A variety of immunoassay formats, including, for example, competitive and non-competitive immunoassay formats, antigen/analyte capture assays, and two-antibody sandwich assays can be used in accordance with the cartridges, kits, and methods described herein. Enzyme-linked immunosorbent assays (ELISAs) can be used in accordance with the present disclosure as well. In the case of an enzyme immunoassay, an enzyme is typically conjugated to a second antibody, generally (for example but not by way of limitation) by means of glutaraldehyde, periodate, hetero-bifunctional crosslinking agents, or biotin-streptavidin complexes. As will be readily recognized, however, a wide variety of different conjugation techniques exist which are readily available for use with the present disclosure to one skilled in the art and thus are also included with the scope of the present disclosure.

Figure 2:
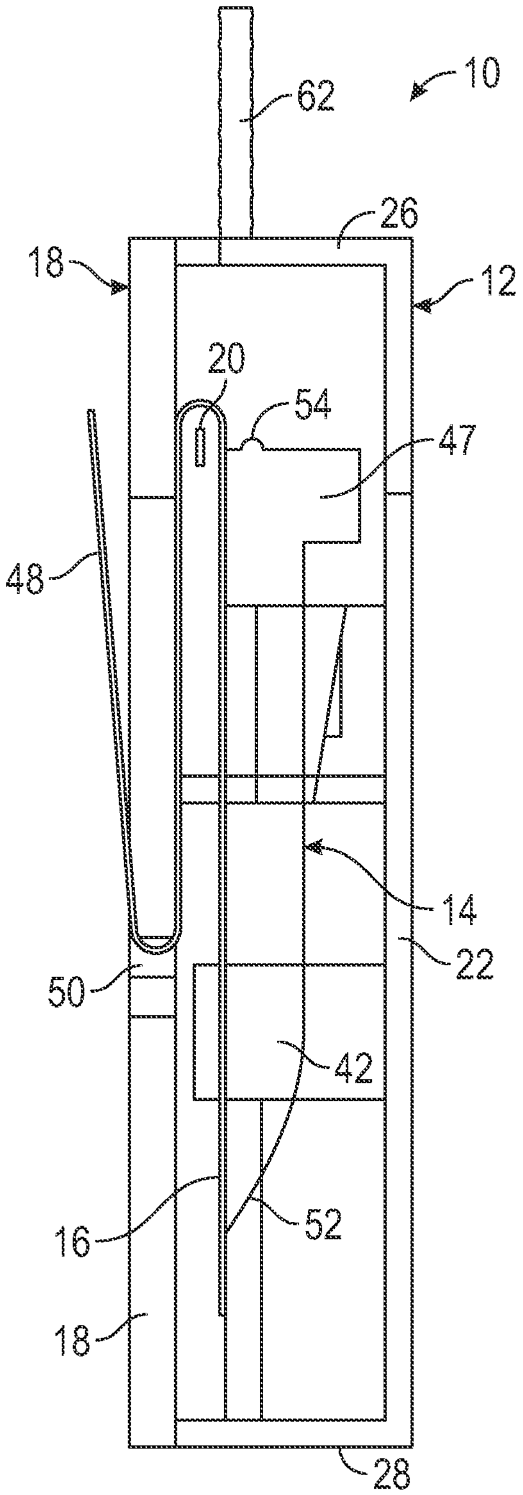
FIG. 2 is a cross-sectional view of the analytical assay reaction cartridge of FIG. 1.
Figure 3:
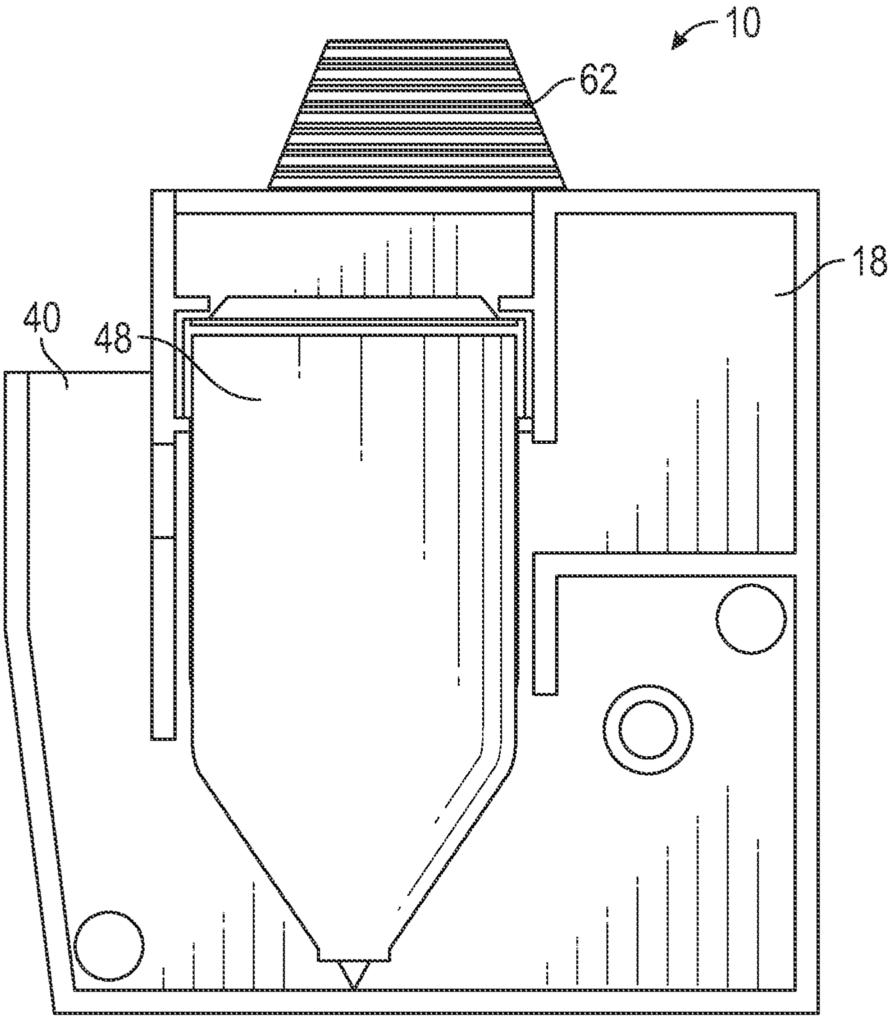
FIG. 3 is a top view of the analytical assay reaction cartridge of FIG. 1.

Referring now to FIGS. 1-3, shown therein is an exploded perspective view of one non-limiting embodiment of an analytical assay reaction cartridge 10 constructed in accordance with the present disclosure. The analytical assay reaction cartridge 10 includes a base 12, a reagent tray 14, a flexible cover 16, a lid member 18, and an optional pivot member 20.

The base 12 includes a back member 22 and a sidewall 24 attached thereto. The sidewall 24 is formed of an upper perimeter side 26, a lower perimeter side 28, a first perimeter side 30, and a second perimeter side 32. The first and second perimeter sides 30 and 32 extend between the upper and lower perimeter sides 26 and 28 and are substantially parallel to one another.

The base 12 also includes a first inner sidewall 34 and a second inner sidewall 36. The first inner sidewall 34 extends perpendicularly from the upper perimeter side 26 and substantially parallel to the first perimeter side 30; in addition, the upper perimeter side 26 has a lower end 35 positioned above the lower perimeter side 28. The second inner sidewall 36 extends perpendicularly from the upper perimeter side 26 and substantially parallel to the second perimeter side 32; in addition, the second inner sidewall 36 has a lower end 37 positioned above the lower perimeter side 28.

The base 12 further includes a reaction chamber 38 defined by a lower portion of the base 12 disposed below the lower ends 35 and 37 of the first and second inner sidewalls 34 and 36, respectively, and formed in between the first and second perimeter sides 30 and 32, respectively, and the lower perimeter side 28.

The base 12 also includes an inlet 40 formed between the first perimeter side 30 and the first inner sidewall 34 for introducing a liquid test sample into the reaction chamber 38. The inlet 40 is substantially parallel to the first perimeter side 30 and the first inner sidewall 34 and extends from the upper perimeter side 26 downward toward the lower perimeter side 28. The inlet 40 is in fluidic communication with (or is capable of being in fluidic communication with) the reaction chamber 38. The inlet 40 is capable of securely receiving a capillary holder (such as, for example (but not by way of limitation) the capillary holder 102 of FIG. 4, as described in detail herein after) and is capable of introducing a liquid test sample from the capillary holder into the reaction chamber 38 of the cartridge 10.

The base 12 may be constructed such that one or more of the components thereof (i.e., the back member 22; the perimeter sides 26, 28, 30, and 32 of the sidewall 24; and the inner sidewalls 34 and 36) are integrally formed as one contiguous piece, for example (but not by way of limitation), one contiguous piece of plastic. Alternatively (and/or in addition thereto), one or more components of the base 12 may be formed separately and then connected to one another via any method known in the art, such as (but not limited to) adhesive(s), glue, sonic welding, laser welding, and/or any type of permanent fastener(s).

The reagent tray 14 is disposed and affixed within the base 12 and secured in place between the first and second inner side walls 34 and 36, respectively. In this manner, the reagent tray 14 is oriented substantially parallel to the first inner sidewall 34 and the second inner sidewall 36. The reagent tray 14 has a cavity 42 in which a predetermined volume of liquid reagent can be disposed. The reagent tray 14 also includes an upper edge 44 that extends around a perimeter of the cavity 42. In addition, in certain non-limiting embodiments, the reagent tray 14 may further include one or more support members, such as the support member 47 shown in FIGS. 1-2, that abuts and/or frictionally engages the back member 22, the first inner sidewall 34, and/or the second inner sidewall 36 of the base 12 (and/or is affixed thereto), for the purpose of securing the reagent tray 14 in position within the reaction cartridge 10.

The flexible cover 16 is removably attached to the upper edge 44 of the reagent tray 14 to seal liquid reagent within the cavity 42 of the reagent tray 14 and thereby form a sealed chamber between the cavity 42 and the flexible cover 16. In addition, the flexible cover 16 has a portion that extends beyond the reagent tray 14 and defines a tab portion 48 which can be pulled to remove a portion or all of the flexible cover 16 from the reagent tray 14 and thereby release the liquid reagent from the reagent tray 14 by allowing for the gravitational dispensing and flow of the liquid reagent into the reaction chamber 38 of the base 12.

The lid member 18 is disposed over the base 12 and sealed to at least a portion of the sidewall 24 of the base 12 so as to seal the reagent tray 14 within the base 12. Such seal can be accomplished via any method commonly known in the art, such as (but not limited to) adhesive(s), glue, sonic welding, laser welding, and/or any type of permanent fastener(s).

In addition, the lid member 18 includes at least one opening 50 through which the tab portion 48 is threaded. The at least one opening 50 is generally disposed at a location that corresponds to being between the first and second inner sidewalls 34 and 36, respectively, and thus is not in contact with the reaction chamber 38.

The pivot member 20 is disposed between the reagent tray 14 and the lid member 18. The tab portion 48 of the flexible cover 16 that extends beyond an upper end 54 of the reagent tray 14 is folded back upon itself around the pivot member 20 so that the tab portion 48 extends through the at least one opening 50 in the lid member 18 in order to facilitate removal of at least a portion of the flexible cover 16 from the reagent tray 14.

In certain non-limiting embodiments, the lid member 18 includes a sample read window 60; generally, the sample read window 60 is located at a position that contacts a portion of the reaction chamber 38. The sample read window 60 can be, by way of example only and not by way of limitation, a transparent cuvette window or an optical window which permits the accurate measurement of detectable assay signals in the area of the sample read window 60.

In certain non-limiting embodiments, the base 12 of the cartridge 10 further includes a flange 62 that generally extends from (for example, but not by way of limitation) a portion of the upper perimeter side 26 of the base 12.

In certain non-limiting embodiments, the analytical assay reaction cartridge 10 may further include at least two guide members for positioning the reagent tray 14 and maintaining same within the base 12 of the analytical assay reaction cartridge 10. For example, the Figures depict a first guide member 64 extending from the first inner sidewall 34 and a second guide member 66 extending from the second inner sidewall 36, and these guide members 64 and 66 frictionally engage the reagent tray 14 and maintain the reagent tray 14 in position within the base 12 of the analytical assay reaction cartridge 10. However, it will be understood that more than two guide members may be present; that is, the analytical assay reaction cartridge 10 may include two guide members, four guide members, six guide members, eight guide members, 10 guide members, 12 guide members, 14 guide members, 16 guide members, 18 guide members, 20 guide members, or more, so long as the combination of guide members are able to function in accordance with the present disclosure.

In certain non-limiting embodiments, these guide members 64 and 66 also extend beyond the flexible cover 16 that is attached to the reagent tray 14; in this manner, the pivot member 20 can frictionally engage the guide members 64 and 66 such that the pivot member 20 is maintained in position within the base 12 of the analytical assay reaction cartridge 10.

While FIGS. 1-3 illustrate the analytical assay reaction cartridge 10 as containing a single reagent tray 14 with a single cavity 42, it will be understood that the reagent tray 14 can contain two or more cavities 42 which contain the same or different reagents, and that the analytical assay reaction cartridge 10 can contain more than two or more reagent trays 14 that contain two or more of the same or different reagents. For example (but not by way of limitation), the reagent tray 14 may be comprised of any number of cavities, such as (but not limited to) 1, 2, 3, 4, 5, 6, 7, 8, 9, 10 or more, or any number of cavities capable of being manufactured for incorporation in the analytical assay reaction cartridge 10 and capable of functioning as described herein. In a similar manner, the analytical assay reaction cartridge may be comprised of any number of reagent trays, such as (but not limited to) 1, 2, 3, 4, 5, 6, 7, 8, 9, 10, or more, or any number of reagent trays capable of being manufactured for incorporation in the analytical assay reaction cartridge 10 and capable of functioning as described herein. As such, the depiction of a single reagent tray with a single cavity is for purposes of illustration only and should not be construed as limiting of the present disclosure.

In addition, one or more additional analytical reagents may be present in the reaction chamber 38 for performing a particular analytical assay procedure. When present, these analytical reagents may be in liquid or solid form. Any analytical reagents present in solid form may be in a substantially dry, water soluble, suspendable, or dissolvable form and can be disposed within the reaction chamber 38, and in certain non-limiting embodiments, incorporated therewithin via any methods known in the art, such as (but not limited to) noncovalent binding techniques, absorptive techniques, and the like. In a particular (but non-limiting) embodiment, these optional solid analytical reagents are in the form of substantially flat, raised portions or mesa-shaped nodes on a surface of a selected area of the back member 22 and/or the sidewall 24 of the base 12 within the reaction chamber 38.

The predetermined volume of the at least one liquid reagent present in the cavity 42 of the reagent tray 14 may be any volume capable of accomplishing the desired functions and assay methods in accordance with the present disclosure; for example (but not by way of limitation), the predetermined volume may be about 0.1 µl, about 0.5 µl, about 1 µl, about 2 µl, about 3 µl, about 4 µl, about 5 µl, about 6 µl, about 7 µl, about 8 µl, about 9 µl, about 10 µl, about 15 µl, about 20 µl, about 25 µl, about 30 µl, about 35 µl, about 40 µl, about 45 µl, about 50 µl, about 55 µl, about 60 µl, about 65 µl, about 70 µl, about 75 µl, about 80 µl, about 85 µl, about 90 µl, about 100 µl, about 125 µl, about 150 µl, about 175 µl, about 200 µl, about 225 µl, about 250 µl, about 275 µl, about 300 µl, about 325 µl, about 350 µl, about 375 µl, about 400 µl, about 425 µl, about 450 µl, about 475 µl, about 500 µl, about 525 µl, about 550 µl, about 575 µl, about 600 µl, about 625 µl, about 650 µl, about 675 µl, about 700 µl, about 725 µl, about 750 µl, about 775 µl, about 800 µl, about 825 µl, about 850 µl, about 875 µl, about 900 µl, about 925 µl, about 950 µl, about 975 µl, about 1 ml, about 2 ml, about 3 ml, about 4 ml, about 5 ml, about 6 ml, about 7 ml, about 8 ml, about 9 ml, about 10 ml, or more. In certain non-limiting examples, the predetermined volume of the liquid analytical reagent falls within a range of two of the above values (i.e., a range of from about 1 µl to about 1 ml, a range of from about 10 µl to about 800 µl, a range of from about 100 µl to about 700 µl, etc.). In one particular (but non-limiting) embodiment, the predetermined volume of the liquid analytical reagent is about 600 µl.

As shown in FIGS. 1-3 and as further described herein, the flexible cover 16 is removably affixed to the reagent tray 14 to seal the cavity 42 and prevent the discharge of the predetermined volume of the liquid reagent from the reagent tray 14. In one non-limiting embodiment, the reagent tray 14 is fabricated as a molded component formed of a rigid plastic material (so as to avoid deformation of the reagent tray 14 upon automatic removal of at least a portion of the flexible cover 16 therefrom when the analytical assay reaction cartridge 10 is placed within a suitable diagnostic assay instrument/system). One non-limiting example of a suitable rigid plastic material from which the reagent tray 14 may be fabricated is high-density polyethylene; however, the reagent tray 14 may be constructed of any material capable of accomplishing the functions described herein. The flexible cover 16 may be, for example and not by way of limitation, constructed of one or more vapor and liquid impermeable material(s), such as (but not limited to) a plastic laminate material and/or aluminum foil material. In one non-limiting embodiment, the flexible cover 16 is selectively affixed to the reagent tray 14 by a heat-activated peelable adhesive that leaves substantially no residue on the reagent tray 14 when a portion or all of the flexible cover 16 is removed from the reagent tray 14.

In one non-limiting embodiment, the flexible cover 16 is fused to the reagent tray 14 such that the flexible cover 16 is fused flush with (or extends beyond) a lower end 52 of the reagent tray 14. The flexible cover 16 extends longitudinally from the lower end 52 to an upper end 54 of the reagent tray 14, the flexible cover 16 being fused to portions or all of the upper edge 44 of the reagent tray 14 surrounding the cavity 42 such that the entirety of the cavity 42 is covered and sealed by the flexible cover 16. In particular, the flexible cover 16 extends past the upper end 54 of the reagent tray 14 by a predetermined length, for folding back upon itself to form the tab portion 48. The predetermined length by which the flexible cover 16 extends beyond the upper end 54 of the reagent tray 14 can be any length capable of accomplishing the functions described herein. For example (but not by way of limitation), the predetermined length of the flexible cover 16 extending past the upper end 54 of the reagent tray 14 may be about 0.1 cm, about 0.2 cm, about 0.3 cm, about 0.4 cm, about 0.5 cm, about 0.6 cm, about 0.7 cm, about 0.8 cm, about 0.9 cm, about 1 cm, about 1.5 cm, about 2 cm, about 2.5 cm, about 3 cm, about 3.5 cm, about 4 cm, about 4.5 cm, about 5 cm, about 5.5 cm, about 6 cm, about 6.5 cm, about 7 cm, about 7.5 cm, about 8 cm, about 9 cm, about 10 cm, about 11 cm, about 12 cm, about 13 cm, about 14 cm, about 15 cm, about 16 cm, about 17 cm, about 18 cm, about 19 cm, about 20 cm, about 21 cm, about 22 cm, about 23 cm, about 24 cm, about 25 cm, about 26 cm, about 27 cm, about 28 cm, about 29 cm, about 30 cm, or more. In certain non-limiting examples, the predetermined length of the flexible cover 16 extending past the upper end 54 of the reagent tray 14 falls within a range of two of the above values (i.e., a range of from about 0.1 cm to about 10 cm, a range of from about 0.5 cm to about 5 cm, etc.

As will be discussed in greater detail herein, the portion of the flexible cover 16 extending past the upper end 54 of the reagent tray 14 may be further configured to facilitate and/or effect the automatic removal of at least a portion of the flexible cover 16 from the reagent tray 14 when the analytical assay cartridge 10 is placed and secured within a suitable diagnostic assay instrument/system. For instance, and as shown in particular in FIG. 2, the portion of the flexible cover 16 extending past the upper end 54 of the reagent tray 14 may be folded back down over the pivot member 20 and up the length of the reagent tray 14 from the upper end 54 to the lower end 52 thereof, and finally threaded through the at least one opening 50 contained within the lid member 18 of the reaction cartridge 10. The tab portion 48 extends through the at least one opening 50, as shown in FIG. 3, for interaction with the diagnostic instrument.

The analytical assay reaction cartridge 10 has a substantially horizontal axis of rotation. In addition, the analytical assay reaction cartridge 10 may be provided with any dimensions that allow the analytical assay reaction cartridge 10 to be disposed within a diagnostic instrument and function as described herein. While the external dimensions of the analytical assay reaction cartridge 10 are not critical, in one non-limiting embodiment, the analytical assay reaction cartridge 10 may be substantially square in shape and have a height and width each in a range of from about 3 cm to about 15 cm and a thickness in a range of from about 0.25 cm to about 2 cm. In one particular (but non-limiting) embodiment, the reaction cartridge 10 is square with dimensions of a height and width of about 6 cm and a thickness of about 1 cm.

Figure 4:
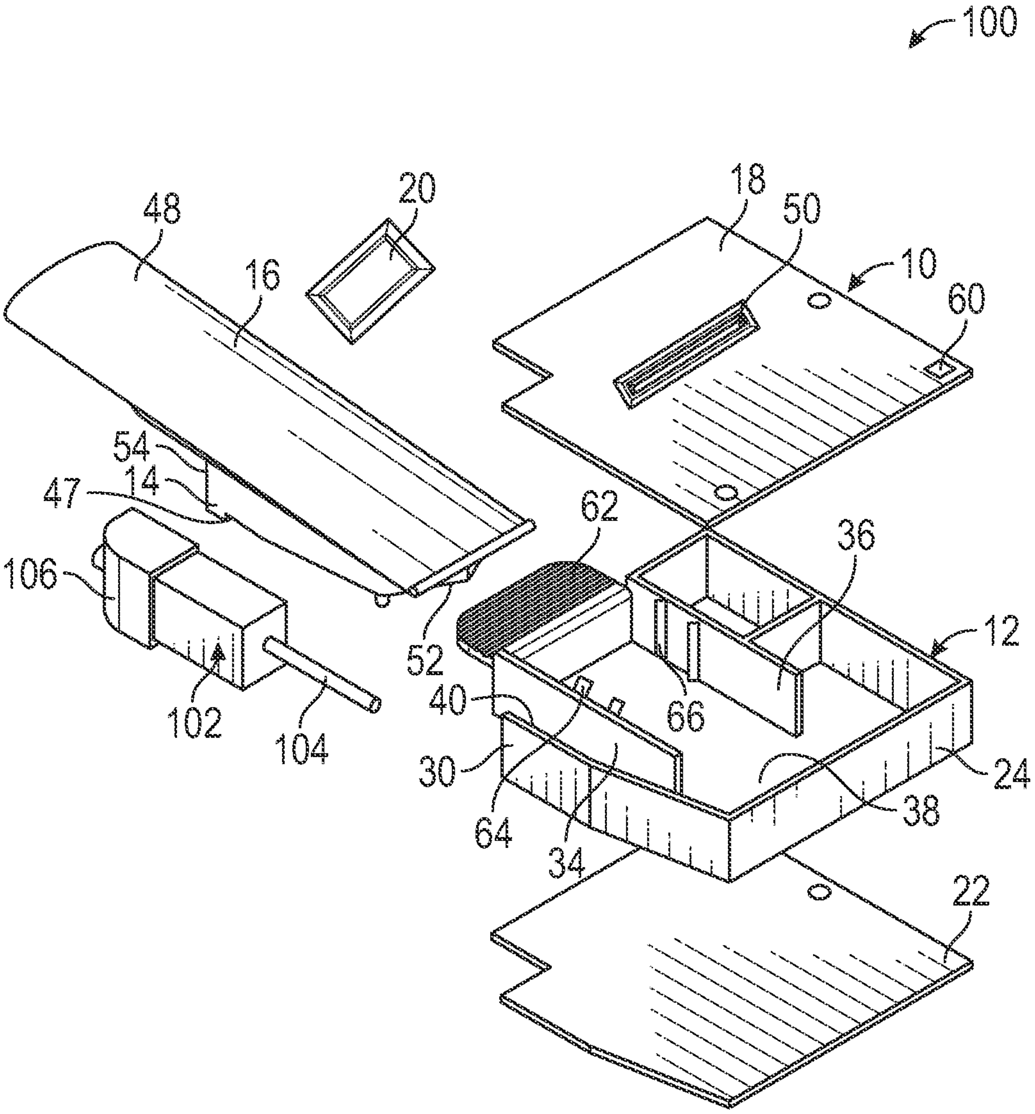
FIG. 4 is an exploded perspective view of a non-limiting embodiment of an analytical assay reaction kit constructed in accordance with the present disclosure and containing the analytical assay reaction cartridge of FIG. 1.

FIG. 4 illustrates an analytical assay reaction kit 100 that includes any of the analytical assay reaction cartridges described or otherwise contemplated herein in combination with a capillary holder 102. FIG. 4 illustrates that the kit 100 includes the analytical assay reaction cartridge 10. However, it will be understood that the kit 100 is not limited to the particular embodiment of the cartridge 10; rather, any cartridges described or otherwise contemplated herein may be utilized in accordance with the present disclosure. As such, the cartridge 10 is depicted in FIG. 4 solely for the purposes of illustrating how the components of the kit 100 interact with one another. Thus, the indications of reference numerals associated with the cartridge of the kit 100 should not be construed as limiting.

The capillary holder 102 is at least partially inserted into the inlet 40 of the analytical assay reaction cartridge 10. In this manner, a liquid test sample can be introduced into the reaction chamber 38 of the cartridge 10, as the inlet 40 is in fluidic communication with the reaction chamber 38.

In certain non-limiting embodiments, the capillary holder 102 includes a capillary 104 into which a portion of the liquid test sample can be drawn. In addition, in certain non-limiting embodiments, the capillary holder 102 may contain additional elements that allow the capillary holder 102 to function in accordance with the present disclosure. For example, but not by way of limitation, the capillary holder 102 may further include an absorbent pad for receiving excess liquid test sample that is drawn into the capillary 104.

In addition, in certain non-limiting embodiments, the capillary holder 102 and/or the first perimeter side 30 and/or the first inner sidewall 34 of the base 12 of the cartridge 10 may be provided with a latching mechanism for securing the capillary holder 102 within the inlet 40 of the cartridge 10. For example (but not by way of limitation), the capillary holder 102 is depicted in FIG. 4 as containing a latching mechanism 106; however, this is for purposes of illustration only, and the cartridge 10 may be provided with a latching mechanism, either alone or in combination with a latching mechanism on the capillary holder 102.

While a capillary holder 102 is shown in FIG. 4 for the purpose of introducing the liquid test sample into the reaction chamber 38 of the reaction cartridge 10, the use of a capillary holder is not to be considered limiting to the present disclosure; it should be readily understood to a person having ordinary skill in the art that the liquid test sample can be introduced into the reaction cartridge 10 via any device(s) known in the art as capable of introducing a liquid test sample into a reaction cartridge, such as (but not limited to) a pipette and the like. In addition, regardless of the mechanism by which the liquid test sample is introduced into the reaction cartridge 10, the inlet 40 can be stoppered, plugged, or otherwise closed subsequent to the introduction of the liquid test sample into the reaction cartridge 10 so as to prevent liquid loss during the course of the assay methodologies described herein. In certain non-limiting embodiments, the capillary holder 102 may be provided with a portion thereof that acts as such a stopper/plug.

Figure 5:
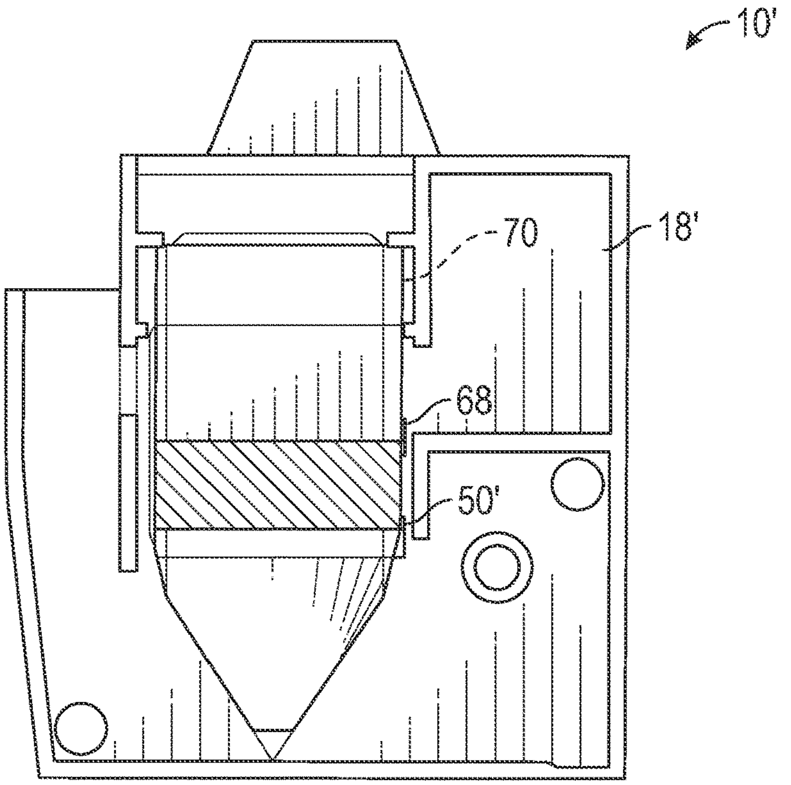
FIG. 5 is a top view of another non-limiting embodiment of an analytical assay reaction cartridge constructed in accordance with the present disclosure.
Figure 6:
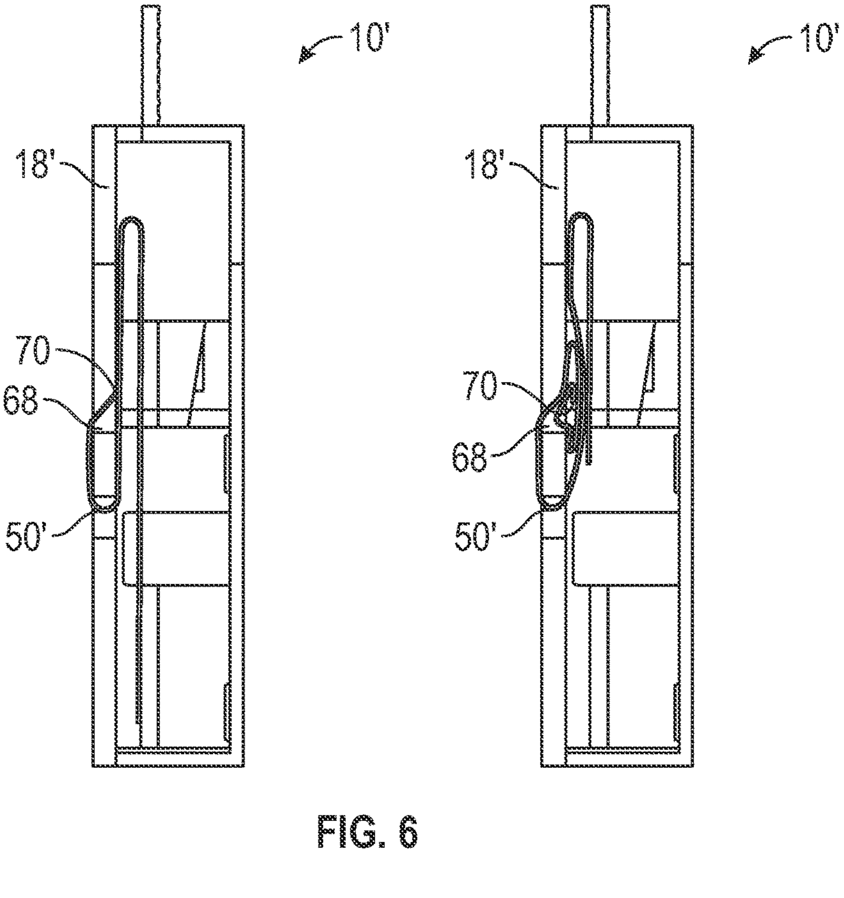
FIG. 6 contains cross-sectional views of the analytical assay reaction cartridge of FIG. 5 prior to (left panel) or following (right panel) actuation of a tab portion of a flexible cover of a reagent tray of the analytical assay reaction cartridge.

As discussed herein above, the lid member of the reaction cartridge can be provided with more than one opening formed therein for threading the tab portion of the flexible cover therethrough. FIGS. 5-6 depict another non-limiting embodiment of an analytical assay reaction cartridge constructed in accordance with the present disclosure and that is identical to the analytical assay reaction cartridge 10 of FIGS. 1-4, except as described herein below. The analytical assay reaction cartridge 10' has a lid member 18' that includes a first opening 50' and a second opening 68. In this embodiment, a tab portion 48' of the flexible cover 16' is first threaded through the first opening 50' and then threaded back through the second opening 68 such that an end 70 of the tab portion 48' is disposed within a base 12' of the cartridge 10'. In this manner, only the portion of the tab portion 48' that extends between the two openings 50' and 68 in the lid member 18' is exposed outside of the analytical assay reaction cartridge 10'. The left panel of FIG. 6 depicts the cartridge 10' prior to actuation of the tab portion 48', while the right panel of FIG. 6 illustrates the cartridge 10' after actuation of the tab portion 48'. As seen in the right panel, a majority of the tab portion 48' can be redirected back into the cartridge 10' for convenient disposal and to prevent the extended portion of the tab portion 48' from interfering with the diagnostic assay or removal of the reaction cartridge 10' from the instrument.

Figure 7:
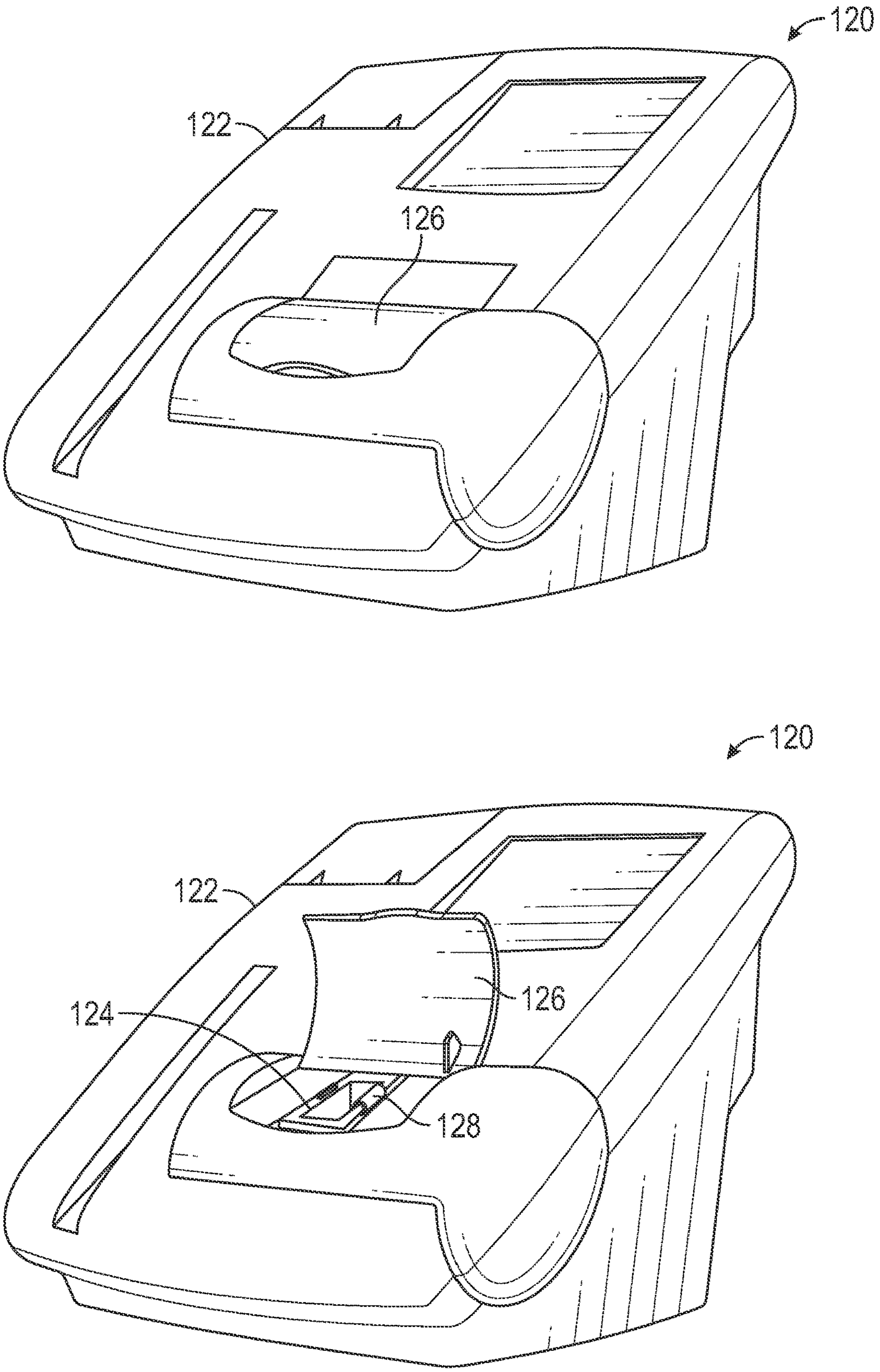
FIG. 7 contains perspective views of a diagnostic instrument constructed in accordance with the present disclosure.

FIG. 7 illustrates a diagnostic assay instrument 120 constructed in accordance with the present disclosure. The diagnostic assay instrument 120 may be a modified version of any diagnostic assay instruments known in the art or otherwise contemplated herein that are utilized with well-known analytical assay reaction cartridges/kits of similar format to those described and contemplated herein, such as (but not limited to) the DCA VANTAGE® analyzer system commercially available from Siemens Healthineers, Inc. (Malvern, PA). The diagnostic assay instrument 120 has a housing 122 that includes at least one cartridge compartment 124 capable of receiving any of the analytical assay reaction cartridges/kits as described or otherwise contemplated herein (such as, but not limited to, the reaction cartridges 10 or 10' or the reaction kit 100). The cartridge compartment 124 is accessible via a door 126 (shown closed in the upper panel of FIG. 7 and open in the lower panel of FIG. 7). The cartridge compartment 124 includes an actuator 128 associated with an upper end or sidewall thereof for interaction with a tab portion of any reaction cartridge/kit described or otherwise contemplated herein; in particular, the actuator 128 grasps and pulls the tab portion of the flexible cover of the reagent tray that extends through the opening in the lid member of the analytical assay reaction cartridge to release the liquid reagent from the reagent tray into the reaction chamber of the cartridge/kit. The diagnostic instrument 120 further includes a detector disposed within the housing 120 for accurately measuring a detectable assay signal in the reaction cartridge/kit; in a particular (but non-limiting) embodiment, the detector measures a detectable assay signal in the area of a sample read window of the reaction cartridge/kit (such as, but not limited to, the sample read window 60 of the reaction cartridge 10 of FIGS. 1 and 4). Detectors useful with the modified diagnostic instrument 120 are well-known in the art, and selection of a detector useful with the reaction cartridges/kits disclosed herein will be well within the purview of a person having ordinary skill in the art; thus, no further discussion thereof is deemed necessary.

In certain non-limiting embodiments, the actuator 128 of the diagnostic assay instrument 120 may be any element having a surface capable of frictionally engaging, grasping, and pulling the exposed tab portion on the outside of any analytical assay reaction cartridge/kit constructed in accordance with the present disclosure. In certain non-limiting embodiments, the actuator 128 comprises at least one tacky surface that contacts the tab portion of a cartridge/kit and that acts as a mechanical wedge that translates the downward force of cartridge/kit insertion into the diagnostic instrument (or a force exerted following cartridge/kit insertion) into lateral pressure on the tab portion that pulls the tab portion further out of the opening in the lid member of the cartridge/kit for releasing the analytical reagent from the reagent tray into the reaction chamber.

In one non-limiting example, the at least one tacky surface of the actuator 128 is a rubber surface or a roughened surface (such as, but not limited to, a rough surfaced metal and/or plastic). In another non-limiting example, the actuator comprises a motorized element (such as, but not limited to, a motorized wheel) that contacts the tab portion after the cartridge is positioned within the instrument.

Certain non-limiting embodiments of the present disclosure are further directed to a method for performing at least one analytical reaction to determine the presence of an analyte in a liquid test sample. In the method, any of the capillary holders described or otherwise contemplated herein is contacted with a liquid test sample, whereby a portion of the liquid test sample is drawn into a capillary of the capillary holder. The capillary holder is then disposed within at least a portion of the inlet of any of the analytical assay reaction cartridges described or otherwise contemplated herein, to thereby introduce the liquid test sample into the reaction chamber of the analytical assay reaction cartridge. The analytical assay reaction cartridge is then positioned within any of the diagnostic assay instruments described or otherwise contemplated herein, wherein the diagnostic instrument includes an actuator that grasps and pulls the tab portion of the flexible cover of the reagent tray that extends through the opening in the lid member of the analytical assay reaction cartridge; in this manner, the predetermined volume of liquid reagent is released from the reagent tray into the reaction chamber (via, for example but not by way of limitation, gravitational dispensing and flow) so that the liquid reagent mixes with the liquid test sample to form a reaction mixture in the reaction chamber. Then, a detectable response in the reaction mixture is measured to determine the presence of at least one analyte in the liquid test sample.

In certain non-limiting embodiments, the detectable response in the reaction mixture is measured through a sample read window in the lid member of the analytical assay reaction cartridge.

In certain non-limiting embodiments, the base of the analytical assay reaction cartridge comprises a flange extending from the upper perimeter side of the base; this flange is utilized for positioning the analytical assay reaction cartridge within the diagnostic assay instrument.

EXAMPLES

Examples are provided hereinbelow. However, the present disclosure is to be understood to not be limited in its application to the specific experimentation, results, and laboratory procedures disclosed herein after. Rather, the Examples are simply provided as one of various embodiments and is meant to be exemplary, not exhaustive.

Example 1: Construction of One Non-Limiting Embodiment of an Analytical Assay Reaction Cartridge A normal buffer tray was filled with 600 μl of solution and then had a ribbon (i.e., a buffer tab) fused to it with heat and pressure to seal in the fluids. The buffer tab was fused flush with the top (thick portion) of the buffer tray and overhangs the bottom (thinner portion) of the buffer tray by about 5-7 inches. The overhang was bent back over the buffer tray with 2-3 inches extending past the top; in this manner, the tab is peeled away from the buffer tray when the tab is pulled flush along the tray. The tray was placed in a cartridge base with its two prong legs fitting into guides in the base. A lid was then sonically welded on top, completing the reaction chamber.

The cartridge differs from currently available cartridges in at least three ways. As can be seen in FIGS. 1-3, a slot/opening has been added into the lid out of the way of the reaction chamber to pass the buffer tab through. Also, as can be seen in FIG. 1, guides have been extended up past the buffer tray. These extended guides hold a novel element which acts as a pivot point for the buffer tab.

As seen in the Figures, the path of the pull tab is as follows: (1) the buffer tray was welded down to the buffer tray; (2) the overhang was folded back over the welded down portion thereof; (3) the buffer tray was placed in the cartridge base; (4) the pivot point was added, and the tab was folded down over it; (5) the tab was threaded through the lid and folded back toward the top.

It is noted that the expected exposed length of the tab portion would be about ½ to about ¼ that shown in FIG. 3.

Example 2: Two-Sample Standard Deviation Test for [Hb] by Condition

Figure 8:
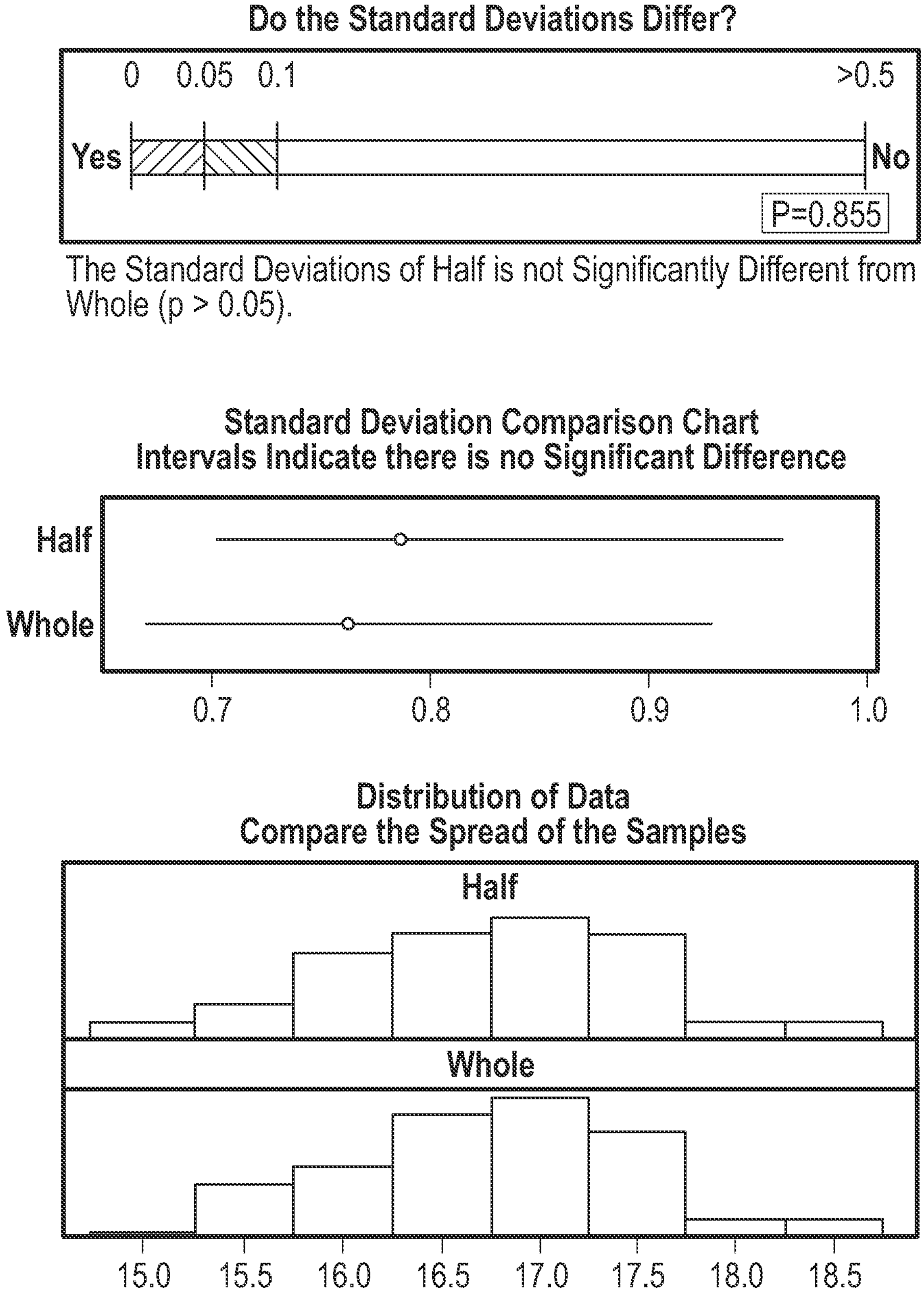
FIG. 8 contains an analysis of a two-sample standard deviation test for [Hb] by condition using prior art analytical assay reaction cartridges and analytical assay reaction cartridges constructed in accordance with the present disclosure.

One of the problems of using existing analytical assay reaction cartridges containing a predetermined volume of liquid reagent, where a tab is manually pulled by a user following insertion of the reaction cartridge into a diagnostic assay instrument, is whether or not all of the reagent is released if the tab is only partially pulled. For experimental analysis of the presently disclosed cartridges (labeled as "Half" in FIG. 8), 32 cartridges were produced that had a 1"×1" window cut out on a laser cutter, and the tab was threaded out through the window. For a control set (labeled as "Whole" in FIG. 8), 32 unmodified cartridges were used.

Both sets of control and experimental cartridges had the FeCN rinsed out with Ro/Di water (twice) and dried overnight at 35° C.; this was done because FeCN is light sensitive and could generate a signal difference due to UV laser exposure.

TS1 (~5.31% HbA1c and 14 g/dL Hb) was run on 30 control cartridges and 30 experimental cartridges. The experimental cartridges were inserted into the instruments before the tabs were pulled; the experimental cartridges only had the tab pulled 1" before getting caught on the lid. The excess exposed tabs were trimmed before running the tests.

When generated [Hb] data is viewed in aggregate (see FIG. 8), there does not appear to be a significant difference in standard deviation. A difference in standard deviation would be expected if buffer/reagent was sporadically remaining in the pucks and increasing the concentration seen with some tests.

TABLE 1

| Statistics | Half | Whole |
|---|---|---|
| Sample Size | 29 | 30 |
| Mean | 16.748 | 16.73 |
| Standard Deviation | 0.78677 | 0.76300 |
| Individual 95% Confidence Interval | (0.6394, 1.038) | (0.6106, 1.020) |

Figure 9:
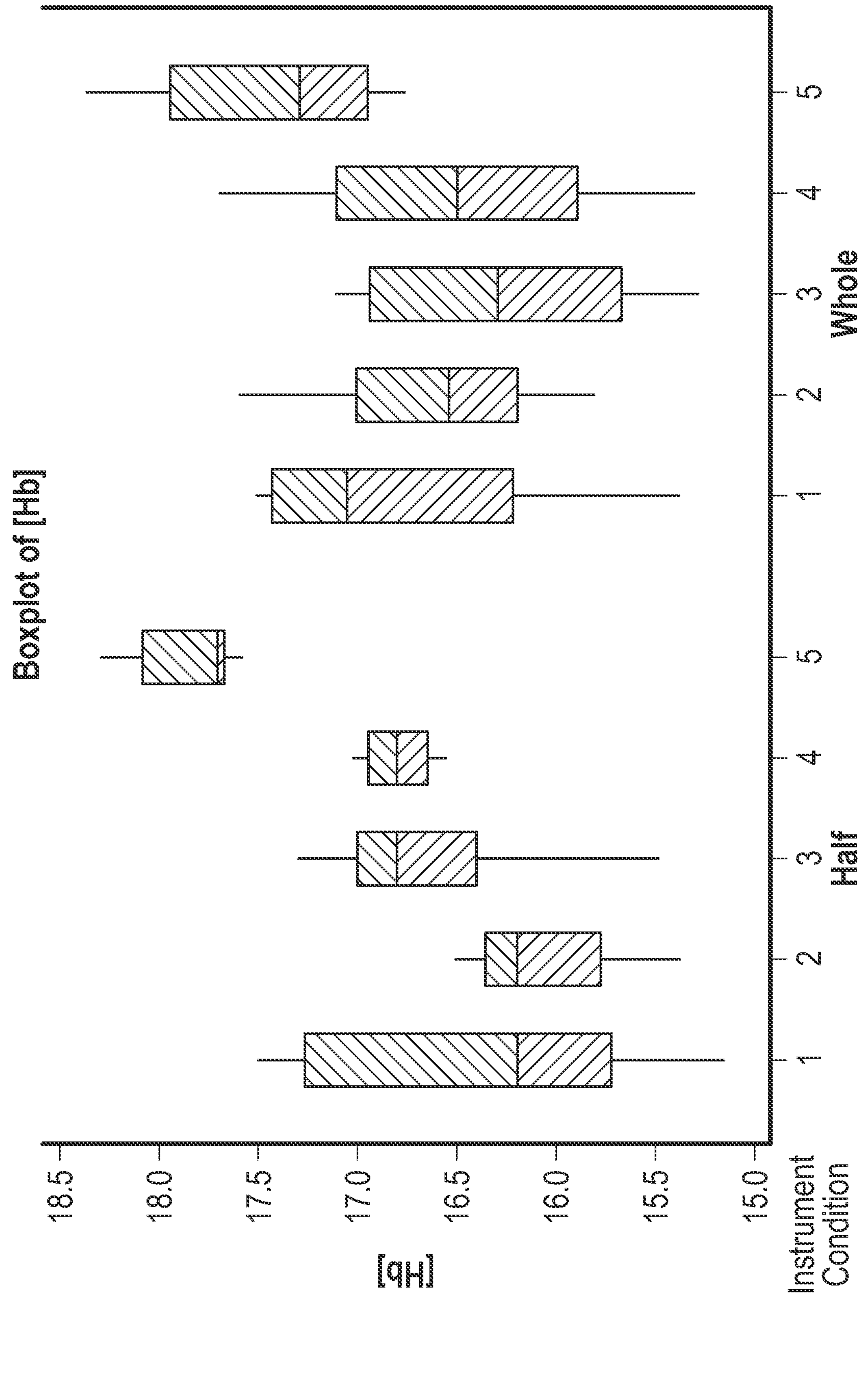
FIG. 9 is a box plot analysis of [Hb] by instrument using analytical assay reaction cartridges constructed in accordance with the present disclosure.

FIG. 9 illustrates a box plot of attachment data by instrument. As can be seen, it appears as though run-to-run instrument variability was reduced when the experimental cartridges were used.

Thus, in accordance with the present disclosure, there have been provided analytical assay reaction cartridges and kits, as well as methods of producing and using same, that fully satisfy the objectives and advantages set forth hereinabove. Although the inventive concept(s) has been described in conjunction with the specific drawings, experimentation, results, and language set forth hereinabove, it is evident that many alternatives, modifications, and variations will be apparent to those skilled in the art. Accordingly, it is intended to embrace all such alternatives, modifications, and variations that fall within the spirit and broad scope of the present disclosure.

What is claimed is:

1. An analytical assay reaction cartridge, comprising:
a base comprising:
a back member;
a sidewall attached to the back member;
a reaction chamber defined by a lower portion of the base;
an inlet for introducing a liquid test sample into the reaction chamber;
a reagent tray disposed and retained within the base, the reagent tray having an upper end, a lower end, a cavity, and an upper edge that extends around a perimeter of the cavity, wherein the cavity is formed to contain a predetermined volume of liquid reagent;
a flexible cover removably attached to the upper edge of the reagent tray to seal the liquid reagent within the cavity and thereby form a sealed chamber between the cavity and the flexible cover, the flexible cover having a portion that extends beyond the upper end of the reagent tray to define a tab portion which can be pulled to remove at least a portion of the flexible cover from the reagent tray and thereby release the liquid reagent into the reaction chamber of the base;
a lid member disposed over the base and sealed to at least a portion of the sidewall of the base so as to seal the reagent tray within the base, the lid member comprising at least one opening through which the tab portion is threaded; and
a pivot member disposed between the reagent tray and the lid member, wherein the tab portion of the flexible cover is folded back upon itself around the pivot member so that the tab portion extends through the at least one opening in the lid member in order to facilitate removal of at least a portion of the flexible cover from the reagent tray for release of substantially all of the liquid reagent into the reaction chamber.

2. The analytical assay reaction cartridge of claim 1, further comprising a sample read window in the lid member at a position that contacts a portion of the reaction chamber.

3. The analytical assay reaction cartridge of claim 1, wherein the lid member comprises a second opening, and wherein the tab portion is threaded back through the second opening such that an end of the tab portion is disposed within the base of the cartridge, and wherein only the portion of the tab portion that extends between the two openings in the lid member is exposed outside of the analytical assay reaction cartridge.

4. The analytical assay reaction cartridge of claim 1, further comprising a predetermined volume of liquid reagent disposed within the cavity of the reagent tray.

5. The analytical assay reaction cartridge of claim 1, wherein the sidewall is formed of an upper perimeter side, a lower perimeter side, a first perimeter side, and a second perimeter side, and wherein the base further comprises:
a first inner sidewall that extends perpendicularly from the upper perimeter side and has a lower end positioned above the lower perimeter side; and
a second inner sidewall that extends perpendicularly from the upper perimeter side and has a lower end positioned above the lower perimeter side.

6. The analytical assay reaction cartridge of claim 5, wherein the reagent tray is retained in place between the first and second inner side walls of the base.

7. The analytical assay reaction cartridge of claim 5, wherein the at least one opening in the lid member is disposed between the first and second inner sidewalls.

8. The analytical assay reaction cartridge of claim 5, wherein the base further comprises a flange extending from the upper perimeter side of the base.

9. The analytical assay reaction cartridge of claim 5, further comprising at least a first guide member extending from the first inner sidewall and a second guide member extending from the second inner sidewall, wherein the guide members frictionally engage the reagent tray and maintain the reagent tray in position within the base of the analytical assay reaction cartridge.

10. The analytical assay reaction cartridge of claim 9, wherein the first and second guide members extend beyond the reagent tray and frictionally engage the pivot member and maintain the pivot member in position within the base of the analytical assay reaction cartridge.

11. An analytical assay reaction kit, the kit comprising:
the analytical assay reaction cartridge of claim 1; and
a capillary holder at least partially inserted into the inlet of the analytical assay reaction cartridge.

12. The analytical assay reaction kit of claim 11, wherein the analytical assay reaction cartridge further comprises a sample read window in the lid member at a position that contacts a portion of the reaction chamber.

13. The analytical assay reaction kit of claim 11, wherein the lid member of the analytical assay reaction cartridge comprises a second opening, and wherein the tab portion is threaded back through the second opening such that an end of the tab portion is disposed within the base of the cartridge, and wherein only the portion of the tab portion that extends between the two openings in the lid member is exposed outside of the analytical assay reaction cartridge.

14. The analytical assay reaction kit of claim 11, wherein the analytical assay reaction cartridge further comprises a predetermined volume of liquid reagent disposed within the cavity of the reagent tray.

15. The analytical assay reaction kit of claim 11, wherein the capillary holder comprises a capillary into which a portion of the liquid test sample can be drawn.

16. The analytical assay reaction kit of claim 11, wherein the sidewall of the analytical assay reaction cartridge is formed of an upper perimeter side, a lower perimeter side, a first perimeter side, and a second perimeter side, and wherein the base further comprises:
a first inner sidewall that extends perpendicularly from the upper perimeter side and has a lower end positioned above the lower perimeter side; and
a second inner sidewall that extends perpendicularly from the upper perimeter side and has a lower end positioned above the lower perimeter side.

17. The analytical assay reaction kit of claim 16, wherein the reagent tray of the analytical assay reaction cartridge is retained in place between the first and second inner sidewalls of the base.

18. The analytical assay reaction kit of claim 16, wherein the at least one opening in the lid member of the analytical assay reaction cartridge is disposed between the first and second inner sidewalls and is not in contact with the reaction chamber.

19. The analytical assay reaction kit of claim 16, wherein the base of the analytical assay reaction cartridge further comprises a flange extending from the upper perimeter side of the base.

20. The analytical assay reaction kit of claim 16, further comprising at least a first guide member extending from the first inner sidewall and a second guide member extending from the second inner sidewall, wherein the guide members frictionally engage the reagent tray and maintain the reagent tray in position within the base of the analytical assay reaction cartridge.

21. The analytical assay reaction kit of claim 20, wherein the first and second guide members extend beyond the reagent tray and frictionally engage the pivot member and maintain the pivot member in position within the base of the analytical assay reaction cartridge.

22. A diagnostic assay instrument, comprising:

a housing that includes at least one cartridge compartment capable of receiving at least one of the analytical assay reaction cartridge of claim 1 or the analytical assay reaction cartridge kit of claim 11;

an actuator associated with the at least one cartridge compartment, wherein the actuator grasps and pulls the tab portion of the flexible cover of the reagent tray that extends through the opening in the lid member of the analytical assay reaction cartridge to release the liquid reagent from the reagent tray into the reaction chamber of the analytical assay reaction cartridge.

23. The diagnostic assay instrument of claim 22, wherein the actuator comprises at least one tacky surface for contacting and pulling the tab portion of the analytical assay reaction cartridge.

24. A method for performing at least one analytical reaction to determine the presence of an analyte in a liquid test sample, the method comprising the steps of:

contacting a capillary holder with a liquid test sample, whereby a portion of the liquid test sample is drawn into a capillary of the capillary holder;

disposing the capillary holder within at least a portion of the inlet of the analytical assay reaction cartridge of claim 1 to thereby introduce the liquid test sample into the reaction chamber of the analytical assay reaction cartridge;

positioning the analytical assay reaction cartridge within a diagnostic assay instrument, wherein the diagnostic assay instrument comprises an actuator that pulls the tab portion that extends through the opening in the lid member of the analytical assay reaction cartridge, thereby releasing the predetermined volume of liquid reagent from the reagent tray into the reaction chamber, whereby the liquid reagent mixes with the liquid test sample to form a reaction mixture in the reaction chamber; and measuring a detectable response in the reaction mixture to determine the presence of at least one analyte in the liquid test sample.

25. The method of claim 24, wherein the actuator of the diagnostic assay instrument comprises at least one tacky surface that contacts the tab portion as the cartridge is being positioned within the instrument.

26. The method of claim 24, wherein the actuator of the diagnostic assay instrument comprises a motorized element that contacts the tab portion after the cartridge is positioned within the instrument.

27. The method of claim 24, wherein the detectable response in the reaction mixture is measured through a sample read window in the lid member of the analytical assay reaction cartridge.

28. The method of claim 24, wherein the base of the analytical assay reaction cartridge comprises a flange extending from the upper perimeter side of the base, wherein the flange is utilized for positioning the analytical assay reaction cartridge within the diagnostic assay instrument.

* * * * *